(12) United States Patent
Whiteley et al.

(10) Patent No.: US 9,596,850 B2
(45) Date of Patent: Mar. 21, 2017

(54) STERILIZING COMPOSITION

(75) Inventors: Reginald Keith Whiteley, North Manly (AU); Marilyn Emily Karaman, Waratah West (AU); Gregory Stuart Whiteley, Queenscliff (AU)

(73) Assignee: #hiteley Corporation PTY. LTD. (AU)

( * ) Notice: Subject to any disclaimer, the term of this patent is extended or adjusted under 35 U.S.C. 154(b) by 1476 days.

(21) Appl. No.: 12/092,042

(22) PCT Filed: Mar. 28, 2008

(86) PCT No.: PCT/AU2008/000436
§ 371 (c)(1),
(2), (4) Date: Jun. 15, 2010

(87) PCT Pub. No.: WO2008/116271
PCT Pub. Date: Oct. 2, 2008

(65) Prior Publication Data
US 2010/0249245 A1    Sep. 30, 2010

(30) Foreign Application Priority Data
Mar. 28, 2007  (AU) ................................ 2007901630

(51) Int. Cl.
*A01N 35/02* (2006.01)
*A01N 35/04* (2006.01)
(Continued)

(52) U.S. Cl.
CPC ............. *A01N 35/02* (2013.01); *A01N 35/04* (2013.01)

(58) Field of Classification Search
CPC .... A01N 35/02; A01N 2300/00; A01N 25/30; A01N 31/02; A01N 33/12; A01N 35/04
(Continued)

(56) References Cited

U.S. PATENT DOCUMENTS

| 5,322,856 A | 6/1994 | Martin |
| 6,380,152 B1 * | 4/2002 | Julemont et al. ............. 510/438 |
| 6,525,101 B2 | 2/2003 | Whiteley |

FOREIGN PATENT DOCUMENTS

| AU | 16302/83 B | 1/1984 |
| AU | WO0207789 | 1/2002 |

(Continued)

OTHER PUBLICATIONS

Machine Translation of DE10012543, accessed on Nov. 16, 2012.*
(Continued)

*Primary Examiner* — Rachael Bredefeld
(74) *Attorney, Agent, or Firm* — Andrew S. Langsam; Pryor Cashman LLP (57) ABSTRACT

Disclosed is a sterilizing composition including (i) at least one mono or dialdehyde; (ii) at least one glycol or polyol or derivative thereof; (iii) a non-ionic first surfactant; and (iv) a second surfactant having a cloud point in the range of about 30° C. to 50° C. Also disclosed is a sterilizing composition including (i) at least one mono or dialdehyde; (ii) at least one glycol or polyol or derivative thereof; (iii) a non-ionic first surfactant; and (iv) a second surfactant, wherein the second surfactant is a quaternary ammonium compound. A process for preparing the compositions of the invention is also disclosed. The compositions of the invention are low or substantially non-foaming under high pressure, high temperature conditions, thus allowing maximum benefit from the new, more reliable, generation of automated endoscope reprocessing machines.

11 Claims, 6 Drawing Sheets

Showing Foam height (%) at 40°C as a function of time (sec) for composition of the invention prepared in Example 1 compared with the control composition given in US 4,748,279 (Note: US 4,748,279 composition denoted by open triangles, the other data given is 3 individual runs of composition of Example 1). Note: Neodol 91-6™ (NLA), Plurafac LF221™ (PLF).

(51) Int. Cl.
*A01N 25/30* (2006.01)
*A01N 31/02* (2006.01)
*A01N 33/12* (2006.01)

(58) Field of Classification Search
USPC .......................................................... 514/693
See application file for complete search history.

(56) References Cited

FOREIGN PATENT DOCUMENTS

| AU | WO2005120592 | | 12/2005 | |
|----|--------------|---|---------|---|
| DE | 10012543 | * | 9/2001 | ............ A01N 35/02 |
| EP | 0596493 B1 | | 2/1999 | |
| EP | 1192860 B1 | | 9/2004 | |
| ID | WO03011027 A1 | | 2/2003 | |
| RU | 2203094 C1 | | 4/2003 | |

OTHER PUBLICATIONS

Ronas Chemical, "Ethoxylated Alcohol, C12-C14," pp. 1-2, http://www.ronaschemical.com/surfactant/PDF%20file/Ethoxylated%20alcohol,C12 -C14%20__2,3,4,7,9E.O__.pdf, Accessed Nov. 18, 2012.*
Zhu et al, "Solvent or Matrix-Mediated 'Molecular Switches,' the Lipophilic Dialdehyde (OPA) and the Amphiphilic 1,3-phthalandiol and OPA Disinfection Mechanism," Current Organic Chemistry, 2005, 9, pp. 1155-1166.*
Material Safety Data Sheet—CIDEX OPA Solution.
Metricide 28 Technical Bulletin.

* cited by examiner

Figure 1: Showing Foam height (%) at 40°C as a function of time (sec) for composition of the invention prepared in Example 1 compared with the control composition given in US 4,748,279 (Note: US 4,748,279 composition denoted by open triangles, the other data given is 3 individual runs of composition of Example 1). Note: Neodol 91-6™ (NLA), Plurafac LF221™ (PLF).

Figure 2: Showing Foam height (%) at 40°C as a function of time (sec) for composition of the invention prepared in Example 2 compared with the control composition given in US 4,748,279. (Note: US 4,748,279 composition denoted by asterisks, the other data given is 4 individual runs of composition of Example 2). Note: Neodol 91-6™(NLA), Antarox LF330™ (ALF).

Figure 3: Showing Foam height (%) at 40°C as a function of time (sec) for composition of the invention prepared in Example 3 compared with the control composition given in US 4,748,279.(Note: US 4,748,279 composition denoted by diamonds, the other data given is 2 individual runs of composition of Example 3). Note: Neodol 91-6™ (NLA), Antarox BL240™ (ABL).

Figure 4: Showing foam height (%) at 40°C as a function of time (sec) for composition of the invention prepared in Example 4 compared with the control composition given in US 4,748,279. (Note: US patent 4,748,279 composition denoted by diamonds and squares, the other data given is 6 individual runs of composition of Example 4). Note: Neodol 91-6™ (NLA), Gardiquat 1450™ (GA)

Figure 5 Showing the % foam height as a function of time (sec) at 40°C for the compositions of the invention MK-13-109(5), MK-13-93(B) and MK-13-108(2) prepared in Example 6.

Figure 6 Showing the % foam height as a function of time (sec) at room temperature for compositions of the invention MK-13-109(5), MK-13-93(B) and MK-13-108(2) prepared in Example 6.

STERILIZING COMPOSITION

FIELD OF THE INVENTION

The present invention relates to compositions and methods useful in the sterilizing of surgical instruments, in particular endoscopic surgical instruments.

BACKGROUND OF THE INVENTION

The cleaning and sterilization of complex endoscopic surgical instruments presents a major problem in achieving a repeatable standard of both cleanliness and biocidal safety.

As the endoscopic instruments used in "key hole surgery" are expanded to cover more types of interventional conventional surgery, new instruments are becoming more and more complex in construction and therefore more difficult to maintain between surgical procedures.

Unfortunately, current endoscope detergents have a problem with foaming under higher pressures. As the complexity of surgical instrument construction has evolved, so has the need for increased miniaturization of tubing systems, through which surgical lighting, instruments, fluids and air are fed to the surgical interface, which has presented problems associated with cleaning efficiency. Cleaning under higher pressures has seen problems associated with reduced cleaning performance which has been further complicated by the need for mechanical cleaning and sterilizing of these complex instruments at temperatures as high as 55° Celsius.

Even further complicating the cleaning procedures is the existence of tenacious and resistant biofilms deposited by bacteria and viruses that enter tubing from the surgical interface. This is particularly the case where surgical instruments have been used to obtain a biopsy from an infected or degenerated wound. Here the contamination may be by bacteria, bacterial spores, fungi, or viruses.

While new high pressure cleaning and sterilizing techniques increase biofilm removal rates, the complexity of circulating systems in endoscopes leads to foam development from surfactants commonly found in the cleaning and sterilizing products used. Foam generated during reprocessing seriously impedes cleaning and biofilm removal.

Thus far, no detergent cleaning product or chemical sterilant has been developed that is both effective as a chemical sterilant and non-foaming under the high pressures exerted within the endoscope tubing and channels during reprocessing.

Existing glutaraldehyde chemical disinfectants, which are commonly used after precleaning with an appropriate medical detergent such as described in WO 02/07789 (inventor R K Whiteley), are an important, effective and economical way of achieving the desired level of disinfection of endoscopes and related instruments. Existing glutaraldehyde chemical compositions include those described in U.S. Pat. No. 4,748,279 and U.S. Pat. No. 6,525,101 (inventor R K Whiteley). However, these existing surfactant compositions suffer from the preceding limitations.

The presence of foam during reprocessing of endoscopic instrument is undesirable as it impedes chemical cleaning and disinfection. The propensity of surfactants to form foams is a distinct area of surfactant science, a subject which is explicitly detailed in terms of physical chemistry and interfacial behaviour discussed in the book by R. Pashley & M. Karaman "Applied Colloid & Surface Chemistry", Wiley press 2004.

Where foams due to surfactants are undesirable, it may be possible to incorporate a small quantity of a second surface active molecule to disrupt the orderly arrangement thus destroying its mechanical stability. This gives a temporary reduction in foam which is often adequate for specific applications. Anti-foam chemicals are also temporary in action and become progressively inactive when solution is reused many times due to the introduction of biological soils (foreign matter).

Surfactants (surface active agents) which are classified as non-foaming are unable to form stable foams because they cannot uniformly pack at the air/water interface. Rather than the surfactant molecules aligning at the air/water interface into a well packed surface layer these surfactants usually have large branched chained moieties which find difficulty in packing at the air/water interface, therefore they have a tendency to lay irregularly across the air/water interface and hence lack the potential to form mechanically stable surface layers. These molecules consequently are unsuitable for formulating disinfectants, chemical sterilants and chemical biocides.

A further method of foam suppression is the addition of a small quantity of a surfactant with a high charge on the hydrophile that is incompatible with that of the primary surfactant. Here the free, more ionized, surfactant molecules compete aggressively for a position at the air/water interface, thereby preventing formation of a stable spatial interfacial surfactant arrangement. The second surfactant contributes little, if anything, to the lowering of the air/water and oil/water interfacial tensions, being totally ineffectual in this latter regard. Foam control is temporarily being readily affected by incoming soil.

The above discussion of background art is included to explain the context of the present invention. It is not to be taken as an admission that any of the documents or other material referred to was published, known or part of the common general knowledge at the priority date of any one of the claims of this specification.

There is a need for a composition which effectively cleans and sterilizes endoscopic surfaces, preferably to a higher standard than is currently achieved. It would be desirable for the composition to be effective at conditions present in washer-disinfectors circulating conditions, which include high temperature (around 35°-55° C.) and high pressure. In particular, the composition must effectively clean and sterilize at temperatures up to 55° C. and high pressure the narrow channels and lumens where fluids and air and/or vacuuming occurs in the endoscopic equipment. Most particularly, the composition should form little or no foam so as to overcome the difficulties encountered with existing compositions during cleaning and sterilising procedures, particularly when cleaning and sterilising endoscopic surgical equipment and instruments.

SUMMARY OF THE INVENTION

The present invention discloses new compositions, with a novel foam control system, that are substantially non-foaming under high pressure conditions, thus allowing maximum benefit from the new, more reliable, generation of automated endoscope reprocessing machines.

The compositions of the present invention are improvements over the compositions described and claimed in U.S. Pat. No. 4,748,279 and U.S. Pat. No. 6,525,101, incorporated herein in their entirety, by reference. As discussed above, the compositions of U.S. Pat. No. 4,748,279 and U.S. Pat. No. 6,525,101, foam in use, especially under high pressure and temperature. As a result, these prior compositions are not well suited to cleaning and sterilising endoscopic surgical equipment and instruments, in automated high temperature high pressure reprocessing.

The compositions of U.S. Pat. No. 4,748,279 and U.S. Pat. No. 6,525,101 include a mono or dialdehyde, glycol or polyol, surfactant and buffer, in demineralised water at a pH of approximately from 6 to 7.2. These compositions foam, which, as discussed above, has particular disadvantages when cleaning some classes of endoscopic equipment. It has now been surprisingly discovered that, by incorporating a particularly selected additional surfactant with compositions such as those described in U.S. Pat. No. 4,748,279 and U.S. Pat. No. 6,525,101, there is a dramatic drop in the amount of foam produced.

In one embodiment, it has been found that, with the particular surfactants therein employed, using an additional surfactant having a cloud point in a particular range dramatically reduces the amount of foam produced. In another embodiment, it has been found that incorporation of quaternary ammonium compound as an additional surfactant dramatically reduces the amount of foam produced.

The composition of the invention demonstrates several extremely useful characteristics. Most importantly it produces very unstable foams even under high pressure cleaning action (eg at temperatures greater than 35° C.); and thus can be successfully employed in high pressure, high temperature type endoscope washing machines. This represents a major advance in medical cleaning technology.

The composition of the invention exhibits superior detergency which is also complementary with increased medical soil removal from endoscope and inanimate surfaces due to significant improved reduction in surface and interfacial tension. Without being bound by theory, it is believed that this improved detergency is due to increased surface activity.

Concomitantly, the reduced odour emission from solutions of the invention compared to other commercially available glutaraldehyde-containing surfactant compositions, is known to be due to increased bonding between the mono/dialdehyde, surfactants and glycol or polyol.

The compositions of this invention produce improved cleaning results from endoscopes thus ensuring a higher standard of reprocessing than in prior compositions. The mono or dialdehyde is also stable. This is a positive when solutions are heated up to 35 to 55° Celsius in endoscope processing systems. Test results on the biological reactive properties of compositions of the invention strongly indicate that the take-up of the biocide by microbes is enhanced when compared with comparative formulations employing more conventional surfactant systems, such as those disclosed in U.S. Pat. Nos. 4,748,279 and 6,525,101. The chemical stability of the mono or dialdehyde composition enables heated sterilising solutions to be recirculated for a period, in excess of 15 days without biocidal or cleaning efficiency being compromised.

Accordingly, there is provided according to a first embodiment of the invention a sterilizing composition including:
(i) at least one mono or dialdehyde;
(ii) at least one glycol or polyol or derivative thereof;
(iii) a non-ionic first surfactant; and
(iv) a second surfactant having a cloud point in the range of about 30° C. to 50° C.

According to a second embodiment of the invention there is provided a sterilizing composition including:
(i) at least one mono or dialdehyde;
(ii) at least one glycol or polyol or derivative thereof;
(iii) a non-ionic first surfactant; and
(iv) a second surfactant, wherein the second surfactant is a quaternary ammonium compound.

The compositions according to the invention are effective in the removal of bacteria, fungi, viruses, and bacterial spores. They may be used in concentrated form, or diluted in a solvent before use. Being substantially non-foaming for practical purposes, the compositions according to the invention are ideally suited to cleaning and sterilisation of reusable surgical appliances or equipment, in particular those used in endoscopic applications.

Accordingly, there is provided according to a third embodiment of the invention a method of destruction or removal of surgical soils from a reusable surgical appliance or equipment, ancillary fibre optic or electronic accessory, which method includes treating the surgical appliance or equipment, ancillary fibre optic or electronic accessory with a composition of the invention.

It has been found that the composition of the invention has a superior capacity to remove the surgical soils.

The invention also relates to processes of preparing the compositions of the invention. The compositions of the invention are prepared by combining the mono or dialdehyde, the glycol or polyol or derivative thereof, the non-ionic first surfactant, and the second surfactant, optionally in a solvent.

Accordingly, there is provided according to a fourth embodiment a process of preparing a sterilizing composition of the first or second embodiments, which process includes combining said at least one mono or dialdehyde, said at least one glycol or polyol or derivative thereof, said non-ionic first surfactant, and said second surfactant.

DETAILED DESCRIPTION OF THE INVENTION

The composition of the invention includes at least one mono or dialdehyde. The mono or dialdehyde preferably contains 2 to 12 carbon atoms which may be mono, di or conjugated alkyl, or substituted or unsubstituted aromatic. A preferred aliphatic dialdehyde used in the composition of the invention is glutaraldehyde. A preferred aromatic dialdehyde used in the composition of the invention is orthophthalaldehyde.

In ready-to-use compositions according to the invention, the mono or dialdehyde is preferably present in an amount of about 0.1 to 3.5 percent by weight of the total weight of the composition. These ready-to-use compositions are typically used for chemical sterilization of surgical instruments and appliances and are useful where fast and efficient disinfecting processes are required. They can also have applications in industrial situations, for example in air conditioning systems and ducting.

In other applications, a composition of the invention having a concentration of about 3.5 to 30 percent mono or dialdehyde, may be prepared. This concentrated composition of the invention may be diluted with, for example, water or a mixture of water and alcohol, to form a diluted composition having about 0.01 to 5.0 percent by weight mono or dialdehyde of the total weight of the composition. This diluted composition is typically used for medical disinfection, such as single shot endoscope washers and tunnel washers, surface disinfection, room disinfection and dental and veterinary hygiene.

The compositions of the invention are effective against biological soil contaminated by bacteria, fungi, viruses, and bacterial spores. As discussed above, test results on the biological reactive properties of compositions of the invention indicate that the take-up of the biocide by microbes is enhanced when compared with formulations such as those disclosed in U.S. Pat. Nos. 4,748,279 and 6,525,101.

The composition of the invention includes at least one glycol or polyol or a derivative thereof, such as glycol ethers and glycol acetates, or a mixture of the glycol, polyol or derivative thereof. Any glycol or polyol which is compatible with the other components of the composition may be included. Preferably, water soluble low molecular weight glycols and their esters having between 2 and 10 carbon atoms, more preferably 4 to 10 carbon atoms, are used. The use of a lower alkanol such as ethanol and isopropanol in part substitution of the glycol also yields solutions which have reasonable stability. However, the lower alkanols may give off unwanted odours and may be flammable in some circumstances and are therefore less preferred.

Preferably, the glycol, polyol or its derivative is selected from ethylene glycol, diethylene glycol, triethylene glycol, tetraethylene glycol, the mono methyl ether of di, tri, or tetraethylene glycol, propylene glycol or mixtures of these.

In a preferred embodiment, about 0.5 to 4.0 mole of glycol or polyol or derivative thereof to about 1 mole of glutaraldehyde in the total weight of the composition is used. In another preferred embodiment, about 14 moles glycol or polyol or derivative thereof to about 1 mole orthophthalaldehyde in the total weight of the composition is used.

The composition of the invention includes a first surfactant which may be selected from the any of the known foaming non-ionic surfactant. Examples of surfactants suitable for use as the first surfactant in the composition of the invention include poly (3-16) ethoxylates of alkyl ($C_8$-$C_{18}$) alkanols, poly (3-16) ethoxylates of alkyl ($C_6$-$C_{14}$) phenols and sulfate and phosphate esters thereof, commercial surfactants derived from block polymers of ethylene and/or propylene oxides with or without small alkyl chain substitutions on the polymer chain or mixtures thereof, and alkyl ($C_8$-$C_{18}$) amine oxides. An example of a high foaming non-ionic surfactant suitable for use in the composition of the invention is an alkyl ($C_8$-$C_{18}$) amine oxide. Preferred is a non-ionic surfactant which contains from 4 to 12 moles of ethylene oxide per non-ionic molecule. Particularly preferred as first surfactant is a $C_9$-$C_{11}$ alcohol ethoxylate containing 6 moles of ethylene oxide per mole of alcohol, sold commercially as Neodol 91-6™.

The composition according to the invention also includes a second surfactant. Surprisingly, it has been found that addition of certain selected surfactants to compositions such as disclosed in U.S. Pat. No. 4,748,279 result in a composition which has substantially no foam, and it therefore highly suited to cleaning and sterilising of surgical equipment and instruments, especially those used in endoscopic applications.

In one embodiment of the invention, the second surfactant has a cloud point in the range of 30° C. to 50° C., more preferably in the range of about 35° C. to 45° C. Second surfactants having a cloud point in this range result in a composition with noticeably diminished foam height over prior art formulations, such as disclosed in U.S. Pat. No. 4,748,279 and U.S. Pat. No. 6,525,101 and with more dynamic foam instability.

In this embodiment, the second surfactant is preferably non-ionic. More preferably the second surfactant having a cloud point in the range 30° to 50° C. is selected from $C_9$-$C_{11}$ alcohol ethoxylate containing 5 moles of ethylene oxide per mole of alcohol, a non-ionic alkoxylated fatty alcohol, an ethoxylated propoxylated $C_8$-$C_{10}$ alcohol, a branched chain chlorine capped ethylene oxide or a polyoxyethylene polyoxypropylene block copolymer.

Examples of commercially available surfactants having a cloud point in the range 30° to 50° C. which are preferred for use as the second surfactant of the invention are Neodol 91-5™ (Shell chemicals) a $C_9$-$C_{11}$ alcohol ethoxylate, Plurafac LF 221™ (BASF) a non-ionic alkoxylated fatty alcohol, Antarox BL240™ (Rhodia) an ethoxylated propoxylated $C_8$-$C_{10}$ alcohol and Antarox LF330™ (Rhodia) a branched chain chlorine capped ethylene oxide and Pluronic PE6200 (BASF), a polyoxyethylene polyoxypropylene block copolymer. An equivalent surfactant to Antarox LF330™ is Teric 165™ (Huntsman).

In another embodiment of the invention, it has been found that use of a quaternary ammonium compound as second surfactant also noticeably diminishes the foam height of the composition of the invention. Use of a quaternary ammonium compound as the second surfactant also results in a composition with noticeably diminished foam height over prior art formulations, such as disclosed in U.S. Pat. No. 4,748,279 and U.S. Pat. No. 6,525,101 and with more dynamic foam instability.

The nitrogen atom of the quaternary ammonium compound is preferably substituted with one or more alkyl groups and one or more phenyl groups. More preferably the nitrogen atom of the quaternary ammonium compound is substituted with one or more methyl groups, a benzyl group and a $C_8$ to $C_{18}$ alkyl group. Of this class of second surfactants, an alkyl $C_{12}$-$C_{16}$ dimethyl benzyl amine halide is preferred. A commercially available quaternary ammonium compound which is particularly preferred is Gardiquat 1450™ (Albright & Wilson).

The composition of the invention typically has a surface tension is less than 30 dynes/cm.

As well as being substantially non-foaming, the compositions of the invention remain clear on storage, indicating that the composition is quite chemically stable. On the other hand, when traditional antifoam compositions were added to the prior art compositions of U.S. Pat. No. 4,748,279 and U.S. Pat. No. 6,525,101 in an effort to reduce the amount of foam, the composition went immediately hazy and was found to be unstable at the levels required to inhibit foaming under higher temperature high pressure conditions. In addition, the foam suppression through the use of traditional antifoams was found to be only temporary in nature.

In a preferred embodiment the composition of the invention includes glutaraldehyde as the dialdehyde and the first and second surfactants are present in a combined amount of about 0.1 to 10 percent by weight of the total weight of the composition. In another preferred embodiment the composition of the invention includes orthophthalaldehyde as the dialdehyde and the first and second surfactants are present in a combined amount of about 0.1 to 30 percent by weight of the total weight of the composition.

The second surfactant may be present in the range 0.5-99.5% by weight of the first surfactant. In one preferred embodiment, the ratio of first surfactant:second surfactant is in the range of about 75:25.

The composition of the invention may further contain a buffer required to control the pH to within the desired biocidal effective range. In a preferred embodiment, where glutaraldehyde is used, the pH is in the range of about 4.0 to about 9.0. In another preferred embodiment, where the orthophthalaldehyde is used, the pH is in the range of about 6 to about 8. These pH ranges ensure sporicidal activity as well as eliminating issues of compatibility of the different components of the composition.

In the composition of the present invention organic acids such as carboxylic acids or derivatised carboxylic acids are useful as buffers. Examples of low molecular weight organic acids useful as buffers and which form reactive salts with monovalent metals are $C_{1-8}$ carboxylic acids and hydroxy-organic acids including but not limited to formates, acetates, lactates, tartrates, citrates, propionates, hydroxyacetates, acetoacetates, acrylates, hydroxymethylacrylates, methylacrylates, benzoates and salicylates. Derivatised carboxylic acids include phosphorylated and sulfhydrylated derivatives and bromosulfamic acid. Thioglycolic acid salts are also active in this regard.

Monovalent salts of simple inorganic acids can be used instead of or in conjunction with organic acids to suit specific circumstances, for example bicarbonates, carbonates, phosphates and silicates. A particularly preferred phosphate is sodium phosphate.

The sterilizing composition of the present invention may optionally include at least one solvent. Any solvent which is compatible with the other components of the composition may be included. For example the solvent may be a small polar solvent.

In a preferred embodiment, the composition of the invention includes at least one solvent selected from any one or more of water, methanol, ethanol, propanol and isopropanol, $C_1$-$C_8$ esters of organic acids and hydroxy organic acids, $C_2$-$C_8$ ketones, mono, di and triglycol ethers containing from 4 to 14 carbon atoms and their molecular variants, aromatic alcohols such as phenol, benzyl alcohol, ethylphenol, phenoxyethanol and nitrogen containing solvents such as pyridine, pyrollidone and their $C_1$-$C_{12}$ derivatives and urea. Examples of other suitable solvents include any of those used in the manufacture of industrial detergents, solvent cleansers, paint strippers and both ink and varnish remover but which are not highly corrosive or toxic or damaging to medical apparatus such as tubing and organic components of endoscopes.

The composition of the invention is prepared by combining at least one mono or dialdehyde, at least one glycol or polyol or derivative thereof, or mixtures of these, and the first and second surfactant. Preferably, the first and second surfactants are cosolubilised before being combined with the other components of the composition. Typically, the at least one polyol or glycol and the first and second surfactants are mixed together, the pH is adjusted into the desired range, and the at least one mono or dialdehyde is then added to the mixture. In a preferred embodiment, where glutaraldehyde is used, the pH is adjusted into the range of about 4 to 9. In another preferred embodiment, where orthophthalaldehyde is used, the pH is adjusted into the range of about 6 to 8.

In use, the compositions according to the invention may be prepared in varying strengths of the active biocide, the mono or dialdehyde, ranging from ready-to-use preparations to more concentrated formulations which are diluted before use.

The ready-to-use compositions, typically used for chemical sterilisation, preferably contain from about 0.1 to 3.5 percent mono or dialdehyde by weight of the total weight of the composition.

Compositions of the invention may be prepared in concentrated form, and then diluted in use. In one preferred embodiment, the concentrated composition contains about 3.5 to 30 percent glutaraldehyde by weight of the total weight of the composition. In another preferred embodiment, the concentrated composition contains about 2.5 to 10 percent orthophthalaldehyde by weight of the total weight of the composition.

In a particularly preferred embodiment, a concentrated composition including about 5 percent by weight of the total weight of the composition of orthophthalaldehyde is prepared.

The concentrated compositions of the invention may be diluted in use, usually with water, buffer or a mixture of water and alcohol. This diluted composition is typically used for medical instrument disinfection.

In a preferred embodiment the diluted composition contains about or 1.5 to 3.5 percent glutaraldehyde by weight of the total weight of the composition.

In another preferred embodiment, the diluted composition contains about 0.01 to about 0.6 percent by weight of the total weight of the composition of orthophthalaldehyde. In yet another preferred embodiment the diluted composition contains about 0.1 to 0.6 percent orthophthalaldehyde by weight of the total weight of the composition.

Compositions according to this invention may be used in instrument disinfection, for example instrument spray washing machines (eg tunnel washers), surface disinfection, room sterilisation and dental and veterinary hygiene. A preferred composition of the invention, used in automated reprocessing of instruments under heated conditions, is prepared by diluting a composition including 0.1 to 1 percent by weight of the total weight of the composition orthophthalaldehyde in the amount of 1 part concentrate to 100 parts water or alcohol, or a mixture thereof. In the case of low temperature automated reprocessing applications, this orthophthalaldehyde composition is preferably diluted to include about 0.5 percent by weight of the total weight of the composition orthophthalaldehyde.

The following examples illustrate some preferred embodiments of the invention. However, it should be understood that the following examples are illustrative only and should not be taken as a restriction on the generality of the invention as described above.

The compositions of Examples 1 to 4 were each based on the formulation disclosed in U.S. Pat. No. 4,748,276, but modifying the quality and type of surfactant to that used in U.S. Pat. No. 4,748,276. The modifications provide a new and practical mechanism of in-situ foam control that provides a substantially non foaming product.

Example 1

Mix in convenient order listed the following ingredients

| Deionised water | 91.9 gram |
|---|---|
| Neodol 9-16 ™ (Shell) | 0.50 gram |
| Plurafac LF-221 ™ (BASF) | 0.40 gram |
| Triethylene glycol | 3.80 gram |
| Plus buffers, dye, | |
| Adjust pH to 6.3-6.5 | |
| 50% medical grade glutaraldehyde | 4.5 gram |

The foam height of this composition of the invention was compared with the foam height of a composition using 100% Neodol 91-6™ (equivalent to the prior art composition disclosed in U.S. Pat. No. 4,748,279). The foam heights obtained for this composition (Neodol 91-6™/Plurac LP221™) were compared with that obtained for the composition disclosed in U.S. Pat. No. 4,748,279. The results are given in FIG. 1.

Figure 1:
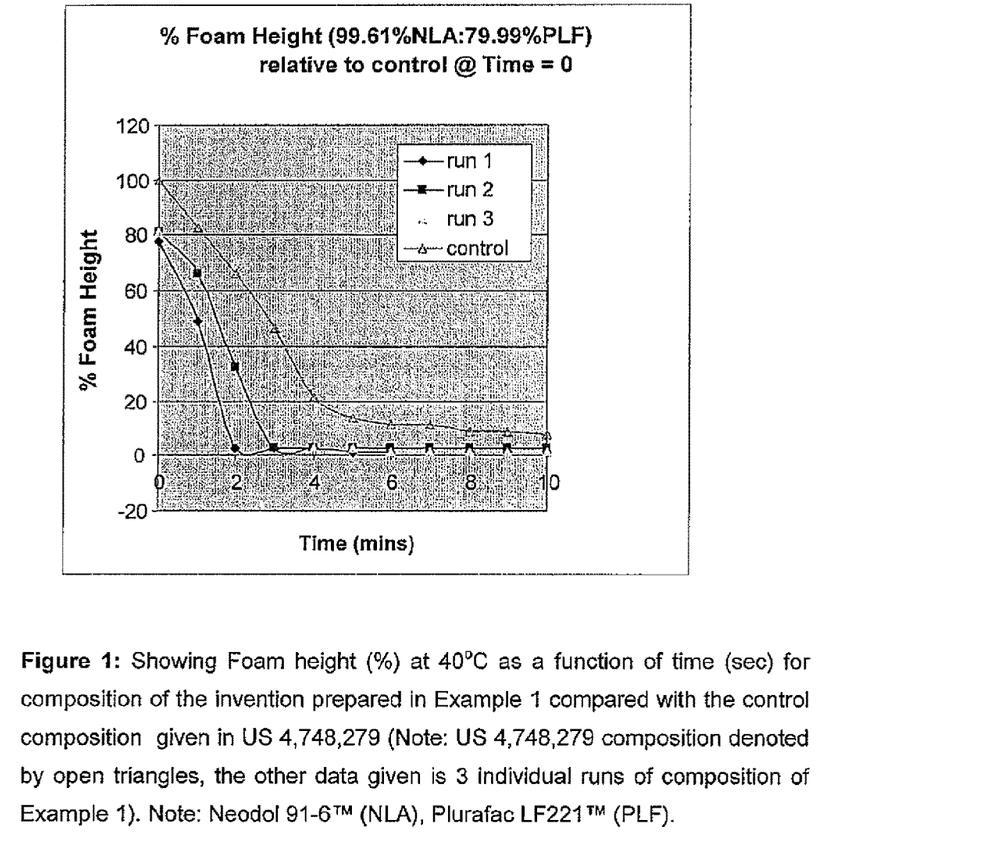
FIG. 1 shows a graph of foam height (%) at 40° C. as a function of time (sec) for the composition of the invention prepared in Example 1 compared with a control composition as per U.S. Pat. No. 4,748,279.

As can be seen, there is a dramatic drop in foam height when 0.4% of Plurafac LF-221™ was added to the composition disclosed in U.S. Pat. No. 4,748,279 (containing Neodol 91-6™) compared to the composition with no Plurafac LF-221™ added.

The surface tension of the composition of the invention was 28.1 dynes cm$^{-1}$. The surface tension of the prior art composition was 28 dynes cm$^{-1}$.

Example 2

The same composition as in Example 1 was prepared, except a 0.5% surfactant concentration was made up of 20% Neodol 91-6™ and 80% Antarox LF330™ (Rhodia).

The foam height of this composition was compared with the foam height of a composition using 100% Neodol 91-6™ (equivalent to the prior art composition disclosed U.S. Pat. No. 4,748,279). The foam heights obtained for this composition (Neodol 91-6™/Antarox LF330™) were compared with that obtained for the composition disclosed in U.S. Pat. No. 4,748,279. The results are given in FIG. 2.

Figure 2:
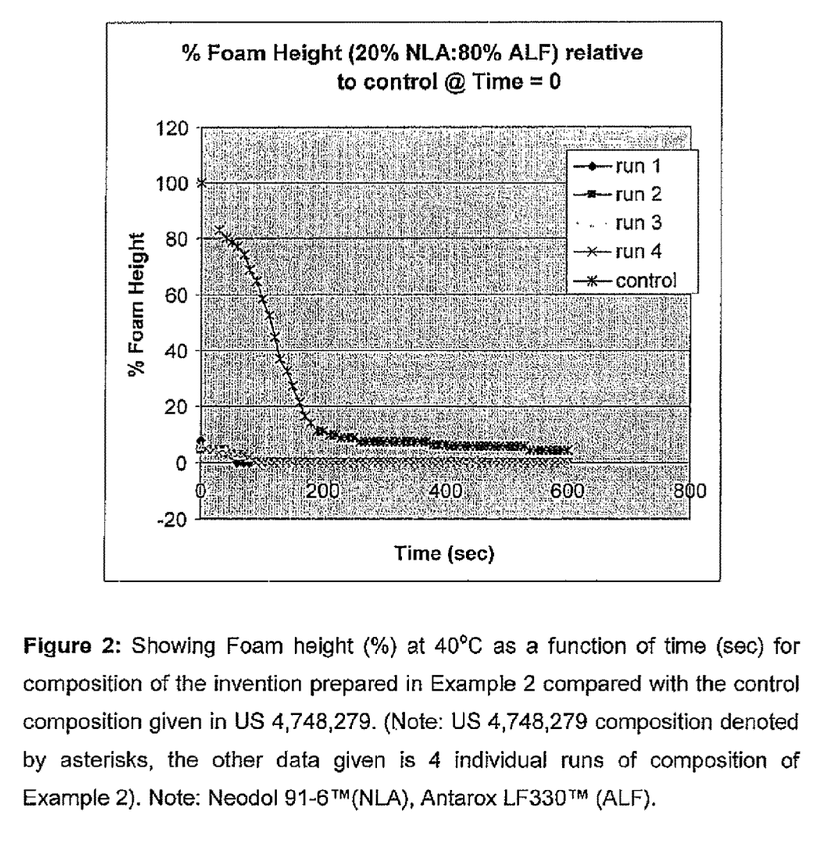
FIG. 2 shows a graph of foam height (%) at 40° C. as a function of time (sec) for the composition of the invention prepared in Example 2 compared with a control composition as per U.S. Pat. No. 4,748,279.

As can be seen, the foam height of the composition of the invention dropped off exceptionally fast when the 0.5% surfactant concentration was made up of, 20% Neodol 91-6™ and 80% Antarox LF330™ as compared to the prior art composition.

The surface tension of the composition of the invention was 22.4 dynes cm$^{-1}$. The surface tension of the prior art composition was 28 dynes cm$^{-1}$.

Example 3

The same composition as in Example 1 was prepared, except a 0.5% surfactant concentration was made up of 20% Neodol 91-6™ and 80% Antarox BL240™ (Rhodia).

The foam height of this composition was compared with the foam height of a composition using 100% Neodol 91-6™ (equivalent to the prior art composition disclosed in U.S. Pat. No. 4,748,279.) The foam heights obtained for this composition (Neodol 9'-6™/Antarox BL240™) were compared with that obtained for the composition disclosed in U.S. Pat. No. 4,748,279. The results are given in FIG. 3.

Figure 3:
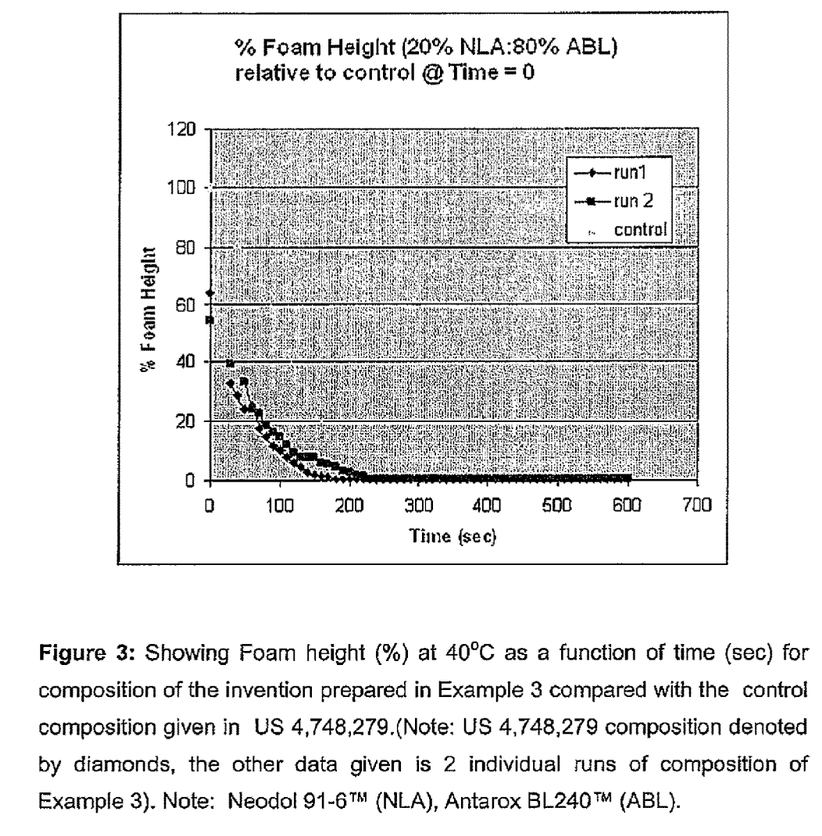
FIG. 3 shows a graph of foam height (%) at 40° C. as a function of time (sec) for the composition of the invention prepared in Example 3 compared with a control composition as per U.S. Pat. No. 4,748,279.

As can be seen, the foam height of the composition of the invention dropped off dramatically when the 0.5% surfactant concentration was made up of 20% Neodol 91-6™ and 80% Antarox LF240™ as compared to the prior art composition.

The surface tension of the composition of the invention was 29.0 dynes cm$^{-1}$. The surface tension of the prior art composition was 28 dynes cm$^{-1}$.

Example 4

The same composition as in Example 1 was prepared, except a 0.5% surfactant concentration was made up of 80% Neodol 91-6™ and 20% Gardiquat 1450™ (Albright & Wilson).

The foam height of this composition was compared with the foam height of a composition using 100% Neodol 916™ (equivalent to the prior art composition disclosed in U.S. Pat. No. 4,748,279.) The foam heights obtained for this composition (Neodol 91-6™/Gardiquat 1450™) were compared with that obtained for the composition disclosed in U.S. Pat. No. 4,748,279. The results are given in FIG. 4.

Figure 4:
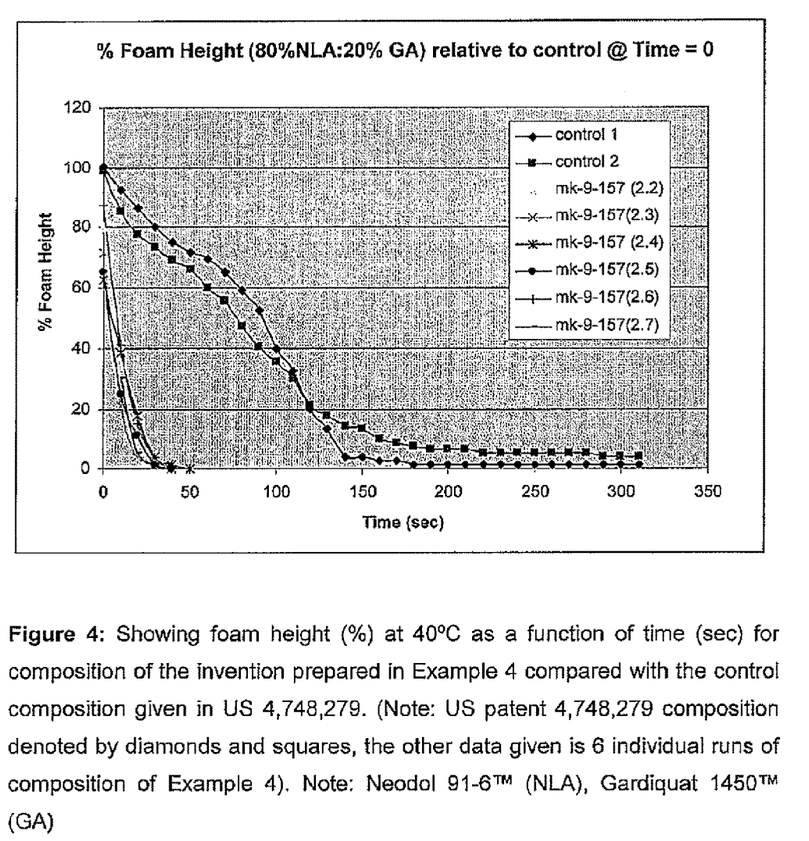
FIG. 4 shows a graph of foam height (%) at 40° C. as a function of time (sec) for the composition of the invention prepared in Example 4 compared with a control composition as per U.S. Pat. No. 4,748,279.

As can be seen, the foam height of the composition of the invention dropped off dramatically when the 0.5% surfactant concentration was made up of 80% Neodol 91-6™ and 20% Gardiquat 1450™ as compared to the prior art composition.

The surface tension of the composition of the invention was 28.1 dynes cm$^{-1}$. The surface tension of the prior art composition was 28 dynes cm$^{-1}$.

Example 5

Compositions of the invention were prepared as set out in Table 1. The compositions of Table 1 are in concentrated form, and typically would be diluted before use.

TABLE 1

| Composition | MK-13-93B (conc) | MK-13-108(2) (conc) | MK-13-109(5) (conc) |
|---|---|---|---|
| Orthophthalaldehyde* | 5.237% | 5.158% | 5.26% |
| Phosphate buffer | Added buffer theoretically pH 8 | Added buffer theoretically pH 8 | Added buffer theoretically pH 8 |
| Isopropylalcohol | — | — | 0.16% |
| Water | 30.01% | 29.99% | 29.94% |
| Propylene glycol | 59.95% | 40.00% | 59.87% |
| Surfactant (1) Neodol 916 | 3.76% | 18.75% | 3.77% |
| Surfactant (2) Pluronic PE6200 | 1.28% | 6.25% | 1.26% |

Note:
*denotes orthophthalaldehyde concentration determined by titrimetric assay The physical characteristics of the compositions of Table 1 are shown in Table 2.

TABLE 2

| Physical Characteristics | MK-13-93B (conc) | MK-13-108(2) (conc) | MK-13-109(5) (conc) |
|---|---|---|---|
| Appearance | Straw coloured solution | Straw coloured solution | Straw coloured solution |
| % w/w Orthophthalaldehyde | 5.237% | 5.158% | 5.26% |
| Odour | Slight | Slight | Slight |
| pH | 7.75 | 7.42 | 7.74 |
| Specific Gravity | 1.0535 | 1.0479 | 1.0535 |
| Refractive Index | 1.4195 | 1.4243 | 1.4199 |

Example 6

Ready-to-use compositions of the invention were prepared by taking the appropriate weight of the concentrate compositions of Example 5 and diluting them with pH 8 sodium phosphate buffer to a given volume. The compositions are given in Table 3.

TABLE 3

| Composition | MK-13-93B (ready to use) | MK-13-108(2) (ready to use) | MK-13-109(5) (ready to use) |
|---|---|---|---|
| Orthophthalaldehyde* | 0.5789% | 0.5796% | 0.5696% |
| Phosphate buffer | Added buffer theoretically pH 8 | Added buffer theoretically pH 8 | Added buffer theoretically pH 8 |
| Isopropylalcohol | — | — | 0.021% |
| Water | 90.8% | 90.8% | 90.76% |
| Propylene glycol | 7.86% | 5.25% | 7.89% |
| Surfactant (1) Neodol 916 | 0.49% | 2.46% | 0.49% |
| Surfactant (2) Pluronic PE6200 | 0.167% | 0.821% | 0.166% |

Note:
*denotes orthophthalaldehyde concentration determined by titrimetric assay The physical characteristics of the compositions of Table 3 are shown in Table 4.

TABLE 4

| Physical Characteristics | MK-13-93B (ready to use) | MK-13-108(2) (ready to use) | MK-13-109(5) (ready to use) |
|---|---|---|---|
| Appearance | Straw coloured solution | Straw coloured solution | Straw coloured solution |
| % w/w Orthophalaldehyde | 0.5789% | 0.5796% | 0.5698% |
| Odour | Slight | Slight | Slight |
| pH | 7.94 | 7.85 | 7.93 |
| Specific Gravity | 1.0138 | 1.013 | 1.0143 |
| Refractive Index | 1.3469 | 1.3482 | 1.3478 |

Figure 5:
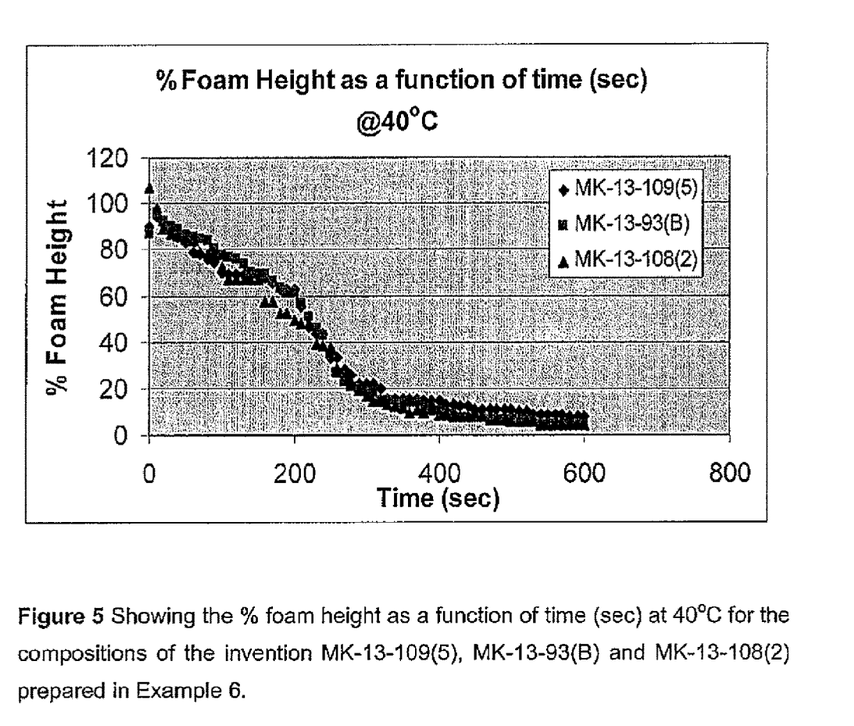
FIG. 5 shows a graph of foam height (%) at 40° C. as a function of time (sec) for the composition of the invention prepared in Example 6.
Figure 6:
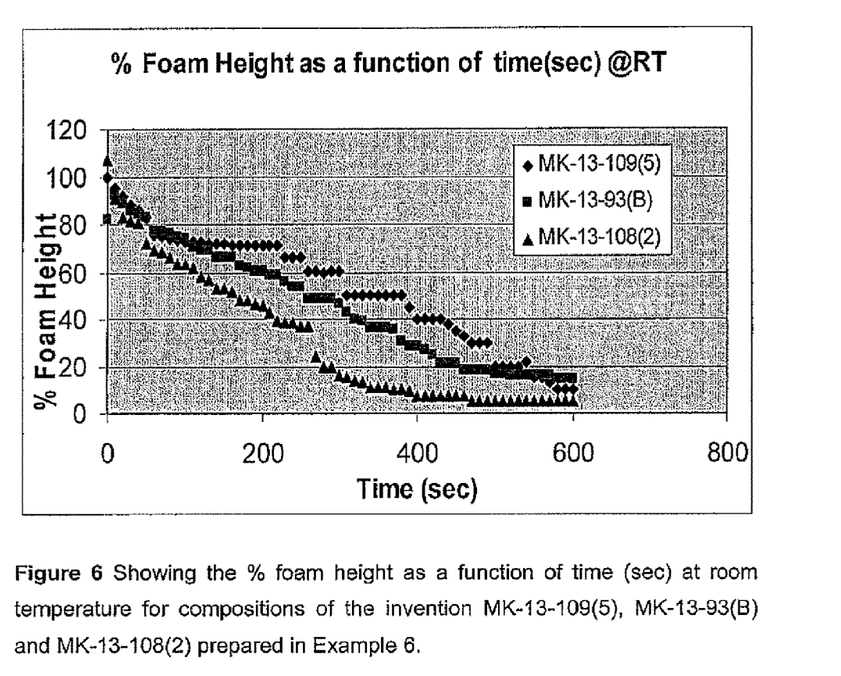
FIG. 6 shows a graph of foam height (%) at room temperature as a function of time (sec) for the composition of the invention prepared in Example 6.

The percent foam height of each of the ready-to-use compositions of Example 6 were measured as a function of time. FIG. 5 shows the percent foam height of each of the ready-to-use formulations MK-13-93B, MK-13-108(2), MK-13-109(5) at 40° C. FIG. 6 shows the percent foam height of each of formulations MK-13-93B, MK-13-108(2), MK-13-109(5) at room temperature.

Example 7

Compositions of the invention were prepared by taking the appropriate weight of the compositions of Example 6 and diluting them with water to give about 0.3% orthophthalaldehyde. The concentration of orthophthalaldehyde in each composition is set out in Table 5. The biocidal properties of these diluted compositions of the invention were compared with those of a commercially available sterilizing solution containing about the same amount of orthophthalaldehyde, Cidex OPA (a product of Johnson & Johnson company). The compositions were tested against *Bacillus subtilis* ATCC19659. The results are set out in Tables 6 and 7. Table 6 shows the number of surviving organisms (cfu/ml) and Table 7 gives the log reduction, for each tested sample.

TABLE 5

| Composition | w/w % orthophthalaldehyde |
|---|---|
| MK-13-93B - diluted | 0.326% |
| MK-13-108 (2) - diluted | 0.321% |
| MK-13-109 (5) - diluted | 0.334% |
| CIDEX OPA | 0.328% |

TABLE 6

| | *B. subtilis* Survivors (cfu/ml) | | | | | |
|---|---|---|---|---|---|---|
| Composition | control | 1 hr | 2 hr | 3 hr | 4 hr | 5 hr |
| MK-13-93B - diluted | 4.3 × 10$^5$ (5.6) | <10 <(1) | <10 <(1) | <10 <(1) | <10 <(1) | <10 <(1) |
| MK-13-108(2) - diluted | | <10 <(1) | <10 <(1) | <10 <(1) | <10 <(1) | <10 <(1) |
| MK-13-109(5) - diluted | | <10 <(1) | <10 <(1) | <10 <(1) | <10 <(1) | <10 <(1) |
| CIDEX OPA | | 5 × 10 (1.7) | <10 <(1) | <10 <(1) | <10 <(1) | <10 <(1) |

TABLE 7

| | *B. subtilis* Log Reduction | | | | | |
|---|---|---|---|---|---|---|
| Composition | control | 1 hr | 2 hr | 3 hr | 4 hr | 5 hr |
| MK-13-93B - diluted | 4.3 × 10$^5$ (5.6) | >4.6 | >4.6 | >4.6 | >4.6 | >4.6 |
| MK-13-108(2) - diluted | | >4.6 | >4.6 | >4.6 | >4.6 | >4.6 |
| MK-13-109(5) - diluted | | >4.6 | >4.6 | >4.6 | >4.6 | >4.6 |
| CIDEX OPA | | 3.9 | >4.6 | >4.6 | >4.6 | >4.6 |

As can be seen, all of the compositions of the invention MK-13-93B, MK-13-108(2), MK-13-109(5) (diluted) have a far better organism kill rate after 1 hour than the commercially available composition.

Example 8

Diluted compositions of the invention containing approximately 0.3% orthophthalaldehyde were prepared and the biocidal properties against *Mycobacteria terrae* were tested using a "Suspension test". Two commercially available solutions, Metricide OPA (Metrex Research Corporation) and Cidex OPA (Johnson & Johnson company), and one internal working control solution (referred to herein as MM_OPA) were also tested against *Mycobacteria terrae* using the same "Suspension test". The Metricide OPA, Cidex OPA and MM_OPA also contained about 0.3% orthophthalaldehyde. The results for the compositions of the invention were compared with those for the three comparative products, Metricide OPA, Cidex OPA and MM_OPA. The results are set out in the following Tables 8 and 9.

As can be seen (with reference to Tables 8 and 9), compositions of the invention MK-13-93B, MK-13-108(2), MK-13-109(5) (0.3% dilution) all achieved favourable results after three minutes, with composition MK-13-108(2) achieving a far better organism kill rate at three minutes than any of the comparative products. Tables 8 and 9 list both the number of surviving organisms (cfu/ml) and the log reduction for each tested sample.

TABLE 8

(comparative compositions)

| | Composition | | | | | | | | | | | |
|---|---|---|---|---|---|---|---|---|---|---|---|---|
| | MM_OPA | | | | Metricide OPA | | | | Cidex OPA | | | |
| | Sample 1 | | Sample 2 | | Sample 1 | | Sample 2 | | Sample 1 | | Sample 2 | |
| Time: | CFU/ml | Log Red. | CFU/ml | Log Red. | CFU/ml | Log Red. | CFU/ml | Log Red. | CFU/ml | Log. Red. | CFU/ml | Log Red. |
| 1 min | TNTC | — | TNTC | — | TNTC | — | TNTC | — | TNTC | — | TNTC | — |
| 3 min | 70 | −4.38535 | 73 | −4.36713 | 10 | −5.23045 | 48 | −4.54921 | 22 | −4.88803 | 24 | −4.85024 |
| 5 min | 0 | >6.2304 | 0 | 0 > 6.2304 | 1 | −6.23045 | 2 | −5.92942 | 1 | −6.23045 | 4 | −6.62839 |
| 7 min | 0 | >6.2304 | 0 | 0 > 6.2304 | 0 | >6.2304 | 0 | >6.2304 | 0 | >6.2304 | 0 | >6.2304 |

TABLE 9

(the invention)

| | Composition | | | | | | | | | | | |
|---|---|---|---|---|---|---|---|---|---|---|---|---|
| | MK-13-93B (diluted) | | | | MK-13-109(5) (diluted) | | | | MK-13-108(2) (diluted) | | | |
| | Sample 1 | | Sample 2 | | Sample 1 | | Sample 2 | | Sample 1 | | Sample 2 | |
| Time: | CFU/ml | Log Red. | CFU/ml | Log Red. | CFU/ml | Log Red. | CFU/ml | Log Red. | CFU/ml | Log.Red. | CFU/ml | Log Red. |
| 1 min | TNTC | — | TNTC | — | TNTC | — | TNTC | — | TNTC | — | TNTC | — |
| 3 min | 11 | −5.18906 | 17 | −5 | 19 | −4.9517 | 34 | −4.69897 | 1 | −6.23045 | 2 | −5.92942 |
| 5 min | 0 | >6.2304 | 1 | −6.23045 | 0 | >6.2304 | 0 | >6.2304 | 0 | >6.2304 | 0 | >6.2304 |
| 7 min | 0 | >6.2304 | 0 | >6.2304 | 0 | >6.2304 | 0 | >6.2304 | 0 | >6.2304 | 0 | >6.2304 |

Footnote:
(Population: 1.86E+07 Innoculation: 1.70E+06)
(TNTC = too numerous to count)

The invention claimed is:

1. A substantially non-foaming sterilizing composition comprising:
   (i) at least one aromatic dialdehyde;
   (ii) at least one glycol or polyol or derivative thereof;
   (iii) a first non-ionic surfactant; and
   (iv) a second surfactant having a cloud point in the range of about 30° C. to 50° C. and selected from the group consisting of an ethoxylated propoxylated C8-C10 alcohol; a branched alcohol ethylene oxide chlorine capped; and a polyoxyethylene polyoxypropylene block copolymer;
   wherein said composition when combined with water has a pH in the range of about 7.40 to 8.0.

2. A sterilizing composition according to claim 1 wherein the first non-ionic surfactant contains from 4 to 12 moles of ethylene oxide per mole of alcohol.

3. A composition according to claim 1 wherein the second surfactant is a polyoxyethylene polyoxypropylene block copolymer.

4. A composition according to claim 1 wherein the aromatic dialdehyde contains 8 to 12 carbon atoms.

5. A composition according to claim 1 wherein the concentration of said aromatic dialdehyde is between 2.5 and 10 percent by weight of the total weight of the composition, and wherein said concentration is intended to be diluted prior to use.

6. A composition according to claim 1, in a ready to use form, wherein the concentration of said aromatic dialdehyde is between 0.1 to 0.6 percent by weight of the total weight of the composition.

7. A composition according to claim 1 wherein said aromatic dialdehyde is orthophthalaldehyde.

8. A composition according to claim 1 wherein said glycol or polyol is present in a ratio of up to 25 mole polyol or glycol to 1 mole of aromatic dialdehyde in the total weight of the composition.

9. A composition according to claim 1, wherein the first and second surfactant are present in a combined amount of about 0.1 to 30 percent by weight of the total weight of the composition.

10. A composition according to claim 1 having a surface tension less than about 30 dynes/cm.

11. A sterilizing composition according to claim 1 wherein the first non-ionic surfactant is selected from the group consisting of poly (3-16) ethoxylates of alkyl (C8-C18) alkanols, poly (3-16) ethoxylates of alkyl (C6-C14) phenols and sulfate and phosphate esters thereof, surfactants derived from block polymers of ethylene and/or propylene oxides with or without small alkyl chain substitutions on the polymer chain or mixtures thereof, and alkyl (C8-C18) amine oxides.

* * * * *

UNITED STATES PATENT AND TRADEMARK OFFICE
CERTIFICATE OF CORRECTION

PATENT NO. : 9,596,850 B2
APPLICATION NO. : 12/092042
DATED : March 21, 2017
INVENTOR(S) : Reginald Keith Whiteley, Marilyn Emily Karaman and Gregory Stuart Whiteley It is certified that error appears in the above-identified patent and that said Letters Patent is hereby corrected as shown below:

On the Title Page (73) Assignee is listed as "#hiteley Corporation PTY. LTD."
Assignee should be "Whiteley Corporation PTY. LTD."

Signed and Sealed this
Tenth Day of July, 2018

Andrei Iancu
*Director of the United States Patent and Trademark Office*